(12) United States Patent
Gordon et al.

(10) Patent No.: US 7,501,473 B2
(45) Date of Patent: *Mar. 10, 2009

(54) AMINOFUNCTIONAL SILICONE RESINS AND EMULSIONS CONTAINING THEM

(75) Inventors: Glenn Gordon, Midland, MI (US); John Bernard Horstman, Midland, MI (US); Donald Liles, Midland, MI (US); Randall Schmidt, Midland, MI (US); Gary Wieber, Midland, MI (US); Gerald Lawrence Witucki, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 412 days.

This patent is subject to a terminal disclaimer.

(21) Appl. No.: 10/564,610

(22) PCT Filed: Jul. 7, 2004

(86) PCT No.: PCT/US2004/021777

§ 371 (c)(1),
(2), (4) Date: Jan. 12, 2006

(87) PCT Pub. No.: WO2005/010076

PCT Pub. Date: Feb. 3, 2005

(65) Prior Publication Data

US 2007/0104674 A1    May 10, 2007

Related U.S. Application Data

(60) Provisional application No. 60/487,698, filed on Jul. 16, 2003.

(51) Int. Cl.
*C08L 83/08* (2006.01)
*C08G 77/26* (2006.01)

(52) U.S. Cl. ............................. 524/838; 528/38; 528/43

(58) Field of Classification Search ........................ None
See application file for complete search history.

(56) References Cited

U.S. PATENT DOCUMENTS

| | | |
|---|---|---|
| 3,166,527 A | 1/1965 | Ender |
| 3,890,269 A | 6/1975 | Martin |
| 4,125,510 A | 11/1978 | Antonen |
| 4,157,357 A | 6/1979 | Mine et al. |
| 4,202,807 A | 5/1980 | Moretto et al. |
| 4,234,697 A | 11/1980 | Homan et al. |
| 4,657,986 A | 4/1987 | Isayama et al. |
| 4,722,951 A | 2/1988 | Yoshioka et al. |
| 4,795,680 A | 1/1989 | Rich et al. |
| 4,857,608 A | 8/1989 | Herzig et al. |
| 4,877,822 A | 10/1989 | Itoh et al. |
| 4,935,482 A | 6/1990 | Decker et al. |
| 4,972,029 A | 11/1990 | Herzig et al. |
| 4,988,778 A | 1/1991 | Chang et al. |
| 5,013,577 A | 5/1991 | Wright et al. |
| 5,102,960 A | 4/1992 | Imai et al. |
| 5,110,891 A | 5/1992 | Cifuentes et al. |
| 5,126,126 A | 6/1992 | Varaprath et al. |
| 5,135,993 A | 8/1992 | Decker et al. |
| 5,152,984 A | 10/1992 | Varaprath et al. |
| 5,262,507 A | 11/1993 | Decker et al. |
| 5,283,279 A | 2/1994 | Hara et al. |
| 5,290,882 A | 3/1994 | Shiobara et al. |
| 5,362,821 A | 11/1994 | Decker et al. |
| 5,378,532 A | 1/1995 | Decker et al. |
| 5,399,652 A | 3/1995 | Bindl et al. |
| 5,405,688 A | 4/1995 | Decker et al. |
| 5,431,765 A | 7/1995 | Decker et al. |
| 5,466,323 A | 11/1995 | Decker et al. |
| 5,489,482 A | 2/1996 | Minemura et al. |
| 5,516,858 A | 5/1996 | Morita et al. |
| 5,561,174 A | 10/1996 | Saito et al. |
| 5,804,616 A | 9/1998 | Mowrer et al. |
| 5,840,806 A | 11/1998 | Komazaki et al. |
| 5,840,951 A | 11/1998 | Hierstetter et al. |
| 5,952,439 A | 9/1999 | Morita et al. |
| 6,071,990 A | 6/2000 | Yip et al. |
| 2006/0205861 A1* | 9/2006 | Gordon et al. ............... 524/506 |
| 2006/0205868 A1* | 9/2006 | Gordon et al. ............... 524/588 |

OTHER PUBLICATIONS

R. Tamaki, J. Choi, and R.M. Lain, A Polyimide Nanocomposite from Octa(aminophenyl)silsesquioxane, Chemical Materials, 2003, pp. 793-797, vol. 15.
C. Li and G. Wilkes, Silicone/Amine Resin Hybrid Materials as Abrasion Resistant Coatings, Chemical Materials, 2001. pp. 3663-3668. vol. 13.

* cited by examiner

*Primary Examiner*—Marc S Zimmer
(74) *Attorney, Agent, or Firm*—Patricia M. Scaduto

(57) ABSTRACT

This invention relates to aminofunctional silicone resins having high aryl content $R_2SiO_{2/2}$ content and amine content. The aminofunctional silicone resins of this invention are useful in making tough, water, solvent, and heat resistant hybrid materials when used in combination with selected organic materials, particularly epoxy-containing organic materials. The aminofunctional resins of this invention have the ability to flexibilize epoxy compounds while maintaining low CTE and solvent resistance. This invention also relates to emulsion compositions containing the above described aminofunctional silicone resins.

20 Claims, No Drawings

AMINOFUNCTIONAL SILICONE RESINS AND EMULSIONS CONTAINING THEM

CROSS REFERENCE TO RELATED APPLICATIONS

This application is a U.S. national stage filing under 35 U.S.C. §371 of PCT Application No. PCT/US2004/021777 filed on Jul. 7, 2004, currently pending, which claims the benefit of U.S. Provisional Patent Application No. 60/487698 filed Jul. 16, 2003 under 35 U.S.C. §119 (e). PCT Application No. PCT/US2004/021777 and U.S. Provisional Patent Application No. 60/487698 are hereby incorporated by reference.

This invention relates to new aminofunctional silicone resins which can be used to make tough, water, solvent and heat resistant hybrid materials with select organic materials. The aminofunctional resins have higher aryl content, $R_2SiO_{2/2}$ content and amine content than those known in the art Aminofunctional silicone resins are known in the art For example, in U.S. Pat. No. 5,262,507 is disclosed an aminofunctional silicone resin comprising the units (i) $PhSiO_{3/2}$, (ii) $R_2SiO$, and (iii) aminofunctional siloxy units selected from the group consisting essentially of a. $H_2NR_iSiO_{3/2}$, b. $R_{iv}HNR_{ii}SiO_{3/2}$, c. $(R_{iv}HNR_{ii})_{3-y}(R_v)_ySiO_{1/2}$, d. $(H_2NR_{ii})_{3-x}(R_v)_xSiO_{1/2}$ and, e. mixtures of a, b, c, and d, wherein Ph is the phenyl radical; each R is independently selected from phenyl and alkyl groups of 1 to 3 carbon atoms with the proviso that when R in (ii) is an alkyl radical in each case, there can be no more than 10 weight percent of (ii) in the silicone resin and with the further proviso that when one R in (ii) is an alkyl radical and one R in (ii) is a phenyl radical on the same silicon atom, there can be no more than 15 weight percent of (ii) present in the silicone resin; $R_i$ is a divalent hydrocarbon radical selected from alkylene, arylene, alkarylene, and aralkylene having 1 to 10 carbon atoms, and —$R_{ii}NHR_{iii}$—, wherein $R_{ii}$ and $R_{iii}$ are each independently selected from alkylene, arylene, alkarylene and aralkylene of 1 to 10 carbon atoms; each of x and y have a value of 0, 1, or 2; $R_{iv}$ is selected from methyl, ethyl, propyl or phenyl; $R_v$ is selected from methyl and phenyl, and the aminofunctional silicone resin has an —NH— equivalent in the range of 350 to 1000.

In U.S. Pat. No. 4,988,778 is disclosed a stable polyamine-functional silane resin which is prepared by reacting: (i) an aminoalkoxysilane and (ii) a hydroxy- and amine-functional compound. The aminoalkoxysilane is disclosed as being typically of the formula: $RNHR^1Si(R^2)_m(OR^3)_n$ wherein R is hydrogen, an alkyl group with no more than four carbon atoms, an aminoalkyl group, alkylamino alkyl group or alkoxysilano alkyl group with no more than 6 carbon atoms in the alkyl group; $R^1$ is an alkylene having 1 to 6 carbon atoms, cycloalkylene or aryl group; $R^2$ is an alkyl having 1 to 10 carbon atoms, cycloalkyl or aryl group; $R^3$ is an lower alkyl group having 1 to about 4 carbon atoms; m is 0 or 1; n is 3 to 2; and m+n=3. Some specific aminoalkoxysilanes disclosed include aminoethyltrimethoxysilane, aminopropyltrimethoxysilane, aminopropyltriethoxysilane, aminopropyldimethoxymethylsilane, aminopropyldiethoxymethylsilane, aminoethyl-gamma-aminopropyltrinmethoxysilane, and iminobis(propyltrimethoxysilane). The hydroxy and amine functional compound is disclosed as being an amino alcohol, amino polyalcohol, a polyamino alcohol or a polyamino polyalcohol.

In U.S. Pat. No. 5,110,891 is disclosed an aminofunctional organosilicon compound of the formula $R_3SiO[R_2SiO]_x[RQ^1SiO]_y[RQSiO]_zSiR_3$ wherein R denotes an alkyl group of one to four carbons, OH, an alkoxy group or a phenyl group with the proviso that at least fifty percent of the total R groups are methyl; Q denotes an amine functional substituent of the formula —$R^2Z$, wherein $R^2$ is a divalent alkylene radical of three to six carbon atoms and Z is a monovalent radical selected from the group consisting —$NR_2^3$, —$NR^3(CH_2)_n NR_2^3$, and —$NR^3(CH_2)_nN(R^3)(C=O)R^4$ wherein $R^3$ denotes hydrogen or an alkyl group of one to four carbons, $R^4$ denotes an alkyl group of one to four carbons and n is an integer from two to six; x, y and z are integers the sum of which is within the range of about twenty-five to about eight hundred; 4 is at least one; and $Q^1$ denotes an amine functional substituent as defined above additionally including a carbon bonded silicon atom having at least one silicon-bonded hydrolyzable group.

In U.S. Pat. No. 5,489,482 is disclosed a film forming composition, comprising an amine-modified highly polymerized polysiloxane represented by the general formula (1): $R_aR'_{3-a}SiO(R_2SiO)_m(RR'SiO)_nSiR_aR'_{3-a}$ wherein R, which are the same or different, each represent a monovalent hydrocarbon group having 1 to 6 carbon atoms, a hydroxyl group, or a hydrogen atom, R' each represent an amino-group-containing organic group, a is an integer of 0 to 3, m is an integer of 1 or more, and n is an integer of 5 or more, provided that m+n is an integer of 2,000 or more, and dissolved in an organic solvent, which film forming composition can give a smooth soft film that is excellent in water repellency, water resistance, touch, and durability in comparison with the conventional film forming compositions.

In U.S. Pat. No. 5,840,951 is disclosed organosilicon compounds containing reactive amino groups, their preparation and their use.

In U.S. Pat. No. 3,890,269 is disclosed a process for preparing amino-functional organopolysiloxanes which comprises equilibrating a mixture containing organopolysiloxane and an aminofunctional silane or siloxane in the presence of a catalyst.

In U.S. Pat. No. 5,152,984 is disclosed an aminofunctional silicone resin comprising the reaction product of an aminofunctional silane and a silicone resin having a formula selected from the group consisting of $RSiO_{3/2}$ (I), $(RSiO_{3/2})_w(R'R''SiO)_x(SiO_{4/2})_y$ (II), and $(RSiO_{3/2})_w(R'R''SiO)_x(SiO_{4/2})_y(R_3'''SiO)_z$ (III)

wherein R, R', R", and R''' are selected from the group consisting of alkyl, alkenyl, aryl, and alkylaryl radicals having from one to twenty carbon atoms; and w, x, y, and z are integers having a value of from zero to about one thousand with the proviso that the sum of w and y is at least one.

In U.S. Pat. No. 5,126,126 is disclosed a hair treating composition comprising a mixture of a film forming material and a solvent for the film forming material, the film forming material being an aminofunctional silicone resin which is the reaction product obtained by directly combining a cyclic silylamine and a silicone resin, the silicone resin being a hydroxy derivative having a formula selected from the group consisting of $RSiO_{3/2}$ (I), $(RSiO3/2)_w(R'R''SiO)_x(SiO_{4/2})_y$ (II), and $(RSiO_{3/2})_w(R'R''SiO)_x(SiO_{4/2})_y(R_3'''SiO_{1/2})_z$ (III)

wherein R, R', R", and R''' are selected from the group consisting of alkyl, alkenyl, aryl, and alkylaryl radicals having from one to twenty carbon atoms; x, y, and z are integers having a value of from zero to about one thousand and w is an integer having a value of from one to about one thousand.

In U.S. Pat. No. 4,972,029 is disclosed thermally stable, crosslinked epoxy resins obtained by crosslinking an epoxy resin with a silicon compound containing a basic nitrogen which is bonded to silicon via carbon and to which at least 1 hydrogen atom is bonded directly to the nitrogen atom, and thereafter conditioning the crosslinked epoxy resin.

Cage structured aminofunctional silicone resins are disclosed in the journal article entitled "A Polyimide Nanocomposite from Octa(aminophenyl)silsesquioxane", R. Tamaki, J. Choi, and R. M. Laine, Chemical Materials, Volume 15, pages 793-797 (2003) and in the journal article entitled "Silicone/Amine Resin Hybrid Materials as Abrasion Resistant Coatings", C. Li and G. Wilkes, Chemical Materials, Volume 13, pages 3663-3668 (2001).

When silicone resins are added to epoxy compounds at high loadings the glass transition temperature of the hybrid material is within the use range and it is accompanied by a large drop in modulus which hinders the reliability of devices based on these materials. Epoxy compounds are brittle and need to be toughened for use in many applications however when linear siloxanes are added to provide greater flexibility the material loses its solvent resistance. Hence there is a need for a material that flexibilizes epoxies while maintaining low CTE and solvent resistance. Thus there is a need for aminofunctional resins with high $R_2SiO$ content>15 mol %, and high amine content.

Thus this invention relates to an aminofunctional silicone resin comprising the units:

$(R_3SiO_{1/2})_a$ (i)
$(R_2SiO_{2/2})_b$ (ii)
$(RSiO_{3/2})_c$ (iii) and
$(SiO_{4/2})_d$ (iv)

wherein R is independently an alkyl group, an aryl group, or an aminofunctional hydrocarbon group, a has a value of less than 0.4, b has a value of greater than 0.15, c has a value of greater than zero to 0.7, d has a value of less than 0.2, the value of a+b+c+d=1, with the provisos that 3 to 50 mole percent of silicon atoms contain aminofunctional hydrocarbon groups in units (i), (ii) or (iii), the —NH— equivalent weight of the aminofunctional silicone resin is from 100 to 1500, alternatively from 100 to 1000, alternatively 150 to 350, the aminofunctional silicone resin is in the form of a neat liquid, solution, or meltable solid, greater than 20 weight percent of unit (ii) is present in the aminofunctional silicone resin, less than 10 weight percent of unit (ii) are $Me_2SiO_{2/2}$ units in the aminofunctional silicone resin, and greater than 50 weight percent of silicon-bonded R groups are silicon-bonded aryl groups.

The —NH— equivalent weight as used herein means the weight of material that contains one atomic weight of amine hydrogen.

The alkyl groups of R are illustrated by methyl, ethyl, propyl, butyl, hexyl, octyl, decyl, dodecyl, hexadecyl, and octadecyl with the alkyl group typically being methyl. The aryl groups are illustrated by phenyl, naphthyl, benzyl, tolyl, xylyl, xenyl, methylphenyl, 2-phenylethyl, 2-phenyl-2-methylethyl, chlorophenyl, bromophenyl and fluorophenyl with the aryl group typically being phenyl. The aminofimctional hydrocarbon group is illustrated by groups having the formula —$R^1NHR^2$ or —$R^1NHR^1NHR^2$ wherein each $R^1$ is independently a divalent hydrocarbon radical having at least 2 carbon atoms and $R^2$ is hydrogen or an alkyl group. Each $R^1$ is typically an alkylene radical having from 2 to 20 carbon atoms. $R^1$ is illustrated by —$CH_2CH_2$—, —$CH_2CH_2CH_2$—, —$CH_2CHCH_3$—, —$CH_2CH_2CH_2CH_2$— —$CH_2CH(CH_3)CH_2$—, —$CH_2CH_2CH_2CH_2CH_2$—, —$CH_2CH_2CH_2CH_2CH_2CH_2$—, —$CH_2CH_2CH(CH_2CH_3)CH_2CH_2$—, —$CH_2CH_2CH_2CH_2CH_2CH_2CH_2CH_2$—, and —$CH_2CH_2CH_2CH_2CH_2CH_2CH_2CH_2CH_2CH_2$—. The alkyl groups $R^2$ are as illustrated above for R. When $R^2$ is an alkyl group it is typically methyl.

Typical aminofunctional hydrocarbon groups are
—$CH_2CH_2NH_2$, —$CH_2CH_2CH_2NH_2$, —$CH_2CHCH_3NH$,
—$CH_2CH_2CH_2CH_2NH_2$, —$CH_2CH_2CH_2CH_2CH_2NH_2$,
—$CH_2CH_2CH_2CH_2CH_2CH_2NH_2$, —$CH_2CH_2NHCH_3$,
—$CH_2CH_2CH_2NHCH_3$, —$CH_2(CH_3)CHCH_2NHCH_3$,
—$CH_2CH_2CH_2CH_2NHCH_3$, —$CH_2CH_2NHCH_2CH_2NH_2$,
—$CH_2CH_2CH_2NHCH_2CH_2NH_2$,
—$CH_2CH_2CH_2CH_2NHCH_2CH_2CH_2NH_2$,
—$CH_2CH_2NHCH_2CH_2NHCH_3$,
—$CH_2CH_2CH_2NHCH_2CH_2NHCH_3$,
—$CH_2CH_2CH_2CH_2NHCH_2CH_2CH_2NHCH_3$, and
—$CH_2CH_2NHCH_2CH_2NHCH_2CH_2CH_3$.

The aminofunctional silicone resins of this invention are illustrated by aminofimctional silicone resins comprising the units:

(i) $((CH_3)_3SiO_{1/2})_a$
(ii) $(C_6H_5(CH_3)SiO_{2/2})_b$
(iii) $((CH_3)RSiO_{2/2})_b$ where R=—$CH_2CH_2CH_2NH_2$
(iv) $(C_6H_5SiO_{3/2})_c$, aminofunctional silicone resins comprising the units:
(i) $(C_6H_5(CH_3)SiO_{2/2})_b$
(ii) $((CH_3)RSiO_{2/2})_b$ where R=—$CH_2CH_2CH_2NH_2$
(iii) $(C_6H_5SiO_{3/2})_c$, aminofunctional silicone resins comprising the units:
(i) $((CH_3)_3SiO_{1/2})_a$
(ii) $((CH_3)RSiO_{2/2})_b$ where R=—$CH_2CH_2CH_2NH_2$
(iii) $(RSiO_{3/2})_c$ where R=—$CH_2CH_2CH_2NH_2$
(iv) $(C_6H_5SiO_{3/2})_c$, aminofunctional silicone resins comprising the units:
(i) $((CH_3)_3SiO_{1/2})_a$
(ii) $((CH_3)RSiO_{2/2})_b$ where R=—$CH_2CH_2CH_2NH_2$
(iii) $(C_6H_5SiO_{3/2})_c$ aminofunctional silicone resin comprising the units
(i) $((CH_3)_3SiO_{1/2})_a$
(ii) $(CH_3)_2SiO_{2/2})_b$
(iii) $((CH_3)RSiO_{2/2})_b$ where R=—$CH_2CH_2CH_2NH_2$
(iv) $(C_6H5SiO_{3/2})_c$ aminofunctional silicone resin comprising the units:
(i) $((CH_3)_2RSiO_{1/2})_a$ where R=—$CH_2(CH_3)CHCH_2NHCH_3$
(ii) $(CH_3)_2SiO_{2/2})_b$
(iii) $(C_6H_5(CH_3)SiO_{2/2})_b$
(iv) $(C_6H_5SiO_{3/2})_c$ aminofunctional silicone resins comprising the units:
(i) $((CH_3)_2RSiO_{1/2})_a$ where R=—$CH_2(CH_3)CHCH_2NHCH_3$
(ii) $(C_6H_5(CH_3)SiO_{2/2})_b$
(iii) $(C_6H_5SiO_{3/2})_c$, aminofimctional silicone resins comprising the units:
(i) $((CH_3)RSiO_{2/2})_b$ where R=—$CH_2(CH_3)CHCH_2NHCH_3$
(ii) $(C_6H_5(CH_3)SiO_{2/2})_b$
(iii) $(C_6H_5SiO_{3/2})_c$, aminofunctional silicone resins comprising the units:
(i) $((CH_3)_2RSiO_{1/2})_a$ where R=—$CH_2(CH_3)CHCH_2NHCH_3$
(ii) $(C_6H_5(CH_3)SiO_{2/2})_b$
(iii) $(SiO_{4/2})_d$, and aminofunctional silicone resins comprising the units:
(i) $((CH_3)_3SiO_{1/2})_a$
(ii) $(C_6H_5(CH_3)SiO_{2/2})_b$ (iii) $((CH_3)RSiO_{2/2})_b$ where $R=$—$CH_2CH_2CH_2NH_2$
(iv) $(C_6H_5SiO_{3/2})_c$
(v) $(SiO_{4/2})_d$ wherein a, b, c, and d are as defined above.

In the aminofunctional silicone resin a has a typical value of 0.1 to 0.3, b has a typical value of 0.2 to 0.4, c has a typical value of 0.2 to 0.5, d has a typical value of 0. Generally, 10 to 30 mole percent of silicon atoms contain aminofunctional hydrocarbon groups in units (i), (ii) or (iii), the —NH— equivalent weight of the aminofunctional silicone resin is generally from 100 to 1500, alternatively from 100 to 1000, alternatively from 150 to 350, generally 20 to 50 weight percent of unit (ii) is present in the aminofunctional silicone resin, generally from 0 to 5 weight percent of unit (ii) are $Me_2SiO_{2/2}$ units in the aminofunctional silicone resin, and generally from 50 to 75 weight percent of silicon-bonded R groups are silicon-bonded aryl groups.

Generally, the aminofunctional silicone resins of this invention were prepared by reaction of a cyclic silazane with a hydroxy-containing siloxane resin or by hydrolytic polycondensation of alkoxysilanes by one of two methods. In some cases, the hydrolysis of the non-aminofunctional alkoxysilanes was accomplished via catalysis with strong acid, followed by addition of the aminofunctional silanes and base-catalyzed equilibration of these species to yield the aminofunctional silicone resin. In other cases, the entire hydrolysis was run under base-catalyzed conditions with the aminofunctional alkoxysilane(s) present from the start. In both cases, the hydrolysis was followed by distillative removal of by-product alcohol, filtration and removal of solvent to provide the product.

More specifically the aminofunctional silicone resins of this invention can be manufactured by preparing a mixture of 45-60 wt % of aryltrialkoxysilane, arylalkyldialkoxysilane, γ-aminoallyltrialkoxysilane, γ-aminoalkyldialkoxysilane and/or γ-aminoalkylmonoalkoxysilane optionally dissolving the mixture in up to 35 wt % of an aromatic solvent This mixture is then hydrolyzed with 1-20 wt % of deionized water, followed by distillative removal of the by-product alcohol. The resulting product is then optionally reacted with up to 50 wt % of trialkylalkoxysilane, hexamethyldisilazane (HMDZ), γ-aminoalkyldialkoxysilane, γ-aminoalkylmonoalkoxysilane and/or dialkyldialkoxysilane, up to 35 wt % of additional solvent, and up to 20 wt % water can be added, a catalytic amount (to make 0-0.1 wt % KOH) of aqueous potassium hydroxide can then be optionally added and the water removed via azeotrope. The hydroxide, if added, is neutralized with aqueous HCl or acetic acid, and water removed again via azeotrope. The mixture is then filtered and solvent removed to yield the aminofunctional silicone resin. Typically the aryl group is phenyl, the alkyl group is methyl, the alkoxy group is either methoxy or ethoxy, and the amino group is the aminofunctional hydrocarbon group described above. The aminofunctional silicone resins of this invention can also be manufactured by hydrolyzing 20-50 wt % of aryltrialkoxysilane and/or arylalkyldialkoxysilane, catalyzed by 0-0.05 wt % with trirluoromethanesulfonic acid (TFMSA), with deionized water (0-10 wt %), followed by distillative removal of by-product alcohol. Up to 35 wt % of hexamethyldisiloxane (HMDS), up to 10 wt % water, and optionally up to 40 wt % toluene is added and the mixture heated to 50-60° C. optionally followed by distillative removal of volatiles. Up to 20 wt % of γ-aminoalkyltrialkoxysilane (APTES), γ-aminoalkylmonoalkoxysilane or γ-aminoalkyldialkoxyalkylsilane are added along with up to 10 wt % water, followed by distillative removal of alcohol. Up to 40 wt % of toluene (if it was not added earlier) is added, up to 10 wt % of water, and optionally a catalytic amount (to make 0-0.1 wt % KOH) of 1.0 N aqueous potassium hydroxide is added and water removed via azeotrope. If added, the hydroxide was neutralized with 1.0 N aqueous HCl or acetic acid, and water again removed via azeotrope. The mixture was filtered and solvent removed to yield the aminofimctional silicone resin. Typically the aryl group is phenyl, the alkyl group is methyl, the alkoxy group is either methoxy or ethoxy, and the amino group is the aminofunctional hydrocarbon group described above.

The aminofunctional silicone resins of this invention can also be manufactured by preparing a mixture of aryltrialkoxysilane, arylalkyldialkoxysilane, and γ-aminoalkyldialkoxyalkylsilane optionally dissolved in xylenes and hydrolyzed with deionized water, followed by distillative removal of by-product alcohol. The resulting product is then reacted with triallylalkoxysilane, additional xylenes and additional water, followed by azeotropic removal of water. To a portion of this reaction mixture, additional xylene and colloidal silica dispersion are added and the water removed via azeotrope. The mixture is filtered and solvent removed to yield the silicone resin. Typically the aryl group is phenyl, the allyl group is methyl, the alkoxy group is either methoxy or ethoxy, and the amino group is the aminofunctional hydrocarbon group described above.

The aminofunctional silicone resins of this invention can also be manufactured by preparing a mixture of aryltrialkoxysilane and arylalkyldialkoxysilane optionally dissolved in xylenes and hydrolyzed with deionized water, followed by distillative removal of by-product alcohol. The resulting product is then reacted with cyclosilazane. The mixture is filtered and solvent removed to yield the silicone resin. Typically the aryl group is phenyl, the alkyl group is methyl, the alkoxy group is either methoxy or ethoxy, and the amino group is the aminofunctional hydrocarbon group described above.

The aminofunctional silicone resins of this invention are useful in making tough, water, solvent, and heat resistant hybrid materials when used in combination with selected organic materials, particularly epoxy-containing organic materials. The aminofunctional resins of this invention have the ability to flexibilize epoxy compounds while maintaining low CTE and solvent resistance.

This invention also relates to an emulsion composition comprising: (A) an aminofunctional silicone resin comprising the units:

$(R_3SiO_{1/2})_a$ (i)
$(R_2SiO_{2/2})_b$ (ii)
$(RSiO_{3/2})_c$ (iii) and
$(SiO_{4/2})_d$ (iv)

wherein R is independently an alkyl group, an aryl group, or an aminofunctional hydrocarbon group, a has a value of less than 0.4, b has a value of greater than 0.15, c has a value of greater than zero to 0.7, d has a value of less than 0.2, the value of a+b+c+d=1, with the provisos that 3 to 50 mole percent of silicon atoms contain aminofunctional hydrocarbon groups in units (i), (ii) or (iii), the —NH— equivalent weight of the aminofunctional silicone resin is from 100 to 1500, alternatively from 100 to 1000, alternatively from 150 to 350, the aminofunctional silicone resin is in the form of a neat liquid, solution, or meltable solid, greater than 20 weight percent of unit (ii) is present in the aminofunctional silicone resin, less than 10 weight percent of unit (ii) are $Me_2SiO_{2/2}$ units in the aminofunctional silicone resin, and greater than 50 weight percent of silicon-bonded R groups are silicon-bonded aryl groups; (B) at least one surfactant; and (C) water.

The aminofunctional silicone resin of Component (A) is as described above including preferred embodiments thereof. The amount of Component (A) in the emulsion composition is typically from 25 to 75 weight percent, said weight percent being based on the total weight of the emulsion composition.

Component (B) is at least one surfactant. The surfactant may be an anionic, cationic, nonionic, or amphoteric surfactant. The surfactants may be employed separately or in combinations of two or more. Examples of suitable anionic surfactants include alkali metal sulforicinates, sulfonated glyceryl esters of fatty acids such as sulfonated monoglycerides of coconut oil acids, salts of sulfonated monovalent alcohol esters such as sodium oleylisethianate, amides of amino sulfonic acids such as the sodium salt of oleyl methyl tauride, sulfonated products of fatty acids nitriles such as palmitonitrile sulfonate, sulfonated aromatic hydrocarbons such as sodium alpha-naphthalene monosulfonate, condensation products of naphthalene sulfonic acids with formaldehyde, sodium octahydroanthracene sulfonate, alkali metal alkyl sulfates such as sodium lauryl sulfate, ammonium lauryl sulfate or triethanol amine lauryl sulfate, ether sulfates having alkyl groups of 8 or more carbon atoms such as sodium lauryl ether sulfate, ammonium lauryl ether sulfate, sodium alkyl aryl ether sulfates, and ammonium alkyl aryl ether sulfates, alkylarylsulfonates having 1 or more alkyl groups of 8 or more carbon atoms, alkylbenzenesulfonic acid alkali metal salts exemplified by hexylbenzenesulfonic acid sodium salt, octylbenzenesulfonic acid sodium salt, decylbenzenesulfonic acid sodium salt, dodecylbenzenesulfonic acid sodium salt, cetylbenzenesulfonic acid sodium salt, and myristylbenzenesulfonic acid sodium salt, sulfiric esters of polyoxyethylene alkyl ether including $CH_3(CH_2)_6CH_2O(C_2H_4O)_2SO_3H$, $CH_3(CH_2)_7CH_2O(C_2H_4O)_{3.5}SO_3H$, $CH_3(CH_2)_8CH_2O(C_2H_4O)_8SO_3H$, $CH_3(CH_2)_{19}CH_2O(C_2H_4O)_4SO_3H$, and $CH_3(CH_2)_{10}CH_2O(C_2H_4O)_6SO_3H$, sodium salts, potassium salts, and amine salts of alkylnaphthylsulfonic acid.

Examples of cationic surfactants include various fatty acid amines and amides and their derivatives, and the salts of the fatty acid amines and amides. Examples of aliphatic fatty acid amines include dodecylamine acetate, octadecylamine acetate, and acetates of the amines of tallow fatty acids, homologues of aromatic amines having fatty acids such as dodecylanalin, fatty amides derived from aliphatic diamines such as undecylimidazoline, fatty amides derived from aliphatic diamines such as undecylimidazoline, fatty amides derived from disubstituted amines such as oleylaminodiethylamine, derivatives of ethylene diamine, quaternary ammonium compounds and their salts which are exemplified by tallow trimethyl ammonium chloride, dioctadecyldimethyl ammonium chloride, didodecyldimethyl ammonium chloride, dihexadecyl ammonium chloride, alkyltrimethylammonium hydroxides such as octyltrimethylammonium hydroxide, dodecyltrimethylammonium hydroxide, or hexadecyltrimethylammonium hydroxide, dialkyldimethylammonium hydroxides such as octyldimethylammonium hydroxide, decyldimethylammonium hydroxide, didodecyldimethylammonium hydroxide, dioctadecyldimethylammonium hydroxide, tallow trimethylammonium hydroxide, coconut oil, trimethylammonium hydroxide, methylpolyoxyethylene cocoammonium chloride, and dipalmrityl hydroxyethylaammonium methosulfate, amide derivatives of amino alcohols such as beta-hydroxylethylstearylamide, and amine salts of long chain fatty acids.

Examples of nonionic surfactants include polyoxyethylene alkyl ethers, polyoxyethylene alkylphenol ethers, polyoxyethylene lauryl ethers, polyoxyethylene sorbitan monoleates, polyoxyethylene alkyl esters, polyoxyethylene sorbitan alkyl esters, polyethylene glycol, polypropylene glycol, diethylene glycol, ethoxylated trimethylnonanols, and polyoxyalkylene glycol modified polysiloxane surfactants.

Examples of the amphoteric surfactants that can be used include amino acid surfactants and betaine acid surfactants.

Typical commercially available surfactants include trimethylnonyl polyethylene glycol ethers and polyethylene glycol ether alcohols containing linear alkyl groups having from 11 to 15 such as 2,6,8-trimethyl-4-nonyloxypolyethylene oxyethadol (6 EO) (sold as Tergitol® TMN-6 by The Dow Chemical Company, Midland, Mich.), 2,6,8-trimethyl-4-nonyloxypolyethylene oxyethanol (10 EO) (sold as Tergitol® TMN-10 by The Dow Chemical Company, Midland, Mich.), alkylene-oxypolyethylene oxyethanol ($C_{11-15}$ secondary alkyl, 9 EO) (sold as Tergitol® 15-S-9 by The Dow Chemical Company, Midland, Mich.), alkylene-oxypolyethylene oxyethanol ($C_{11-15}$ secondary alkyl, 15 EO) (sold as Tergito® 15-S-15 by The Dow Chemical Company, Midland, Mich.), octylphenoxy polyethoxy ethanols having varying amounts of ethylene oxide units such as octylphenoxy polyethoxy ethanol (40 EO) (sold as Tritong® X405 by Rohm and Haas Company, Philadelphia, Pa.), nonionic ethoxylated tridecyl ethers available from Emery Industries, Mauldin, S.C. under the general tradename Trycol, alkali metal salts of dialkyl sulfosuccinates available from American Cyanamid Company, Wayne, N.J. under the general tradename Aerosol, polyethoxylated quaternary ammonium salts and ethylene oxide condensation products of the primary fatty amines, available from Armak Company, Chicago, Ill. under the tradenames Ethoquad, Ethomeen, or Arquad, and polyoxyalkylene glycol modified polysiloxanes. These preferred surfactants may also be obtained from other suppliers under different tradenames.

Surfactants useful in the invention also include those derived from silicone, sorbitan derivatives, and fatty alcohol derivatives. More specifically, suitable surfactants include, but are not limited to, sorbitan sesquioleate, sorbitan oleate, sorbitan isostearate; alkoxylated alcohols such as ethoxylated fatty alcohols including laureth-4, laureth-7, deceth-12, steareth-10; hydroxylated derivatives of polymeric silicones, such as dimethicone copolyol; alkylated derivatives of hydroxylated polymeric silicones such as cetyl dimethicone copolyol; glyceryl esters such as polyglyceryl-4-isostearate; and mixtures thereof, especially mixtures of hydroxylated derivatives of polymeric silicones, alkylated derivatives of hydroxylated polymeric silicones and glyceryl esters, most especially mixtures of dimethicone copolyol, cetyl dimethicone copolyol and polyglyceryl-4-isostearate. Most preferred is a mixture of such surfactants, i.e. a dimethicone copolyol, sorbitan sesquioleate and laureth-7.

The amount of Component (B) in the emulsion composition is typically from 1 to 20 weight percent, said weight percent being based on the total weight of the emulsion composition.

Component (C) is water. Generally water is present at a level of from about 20 to 80 weight percent, said weight percent being based on the total weight of the emulsion composition.

The emulsion compositions of this invention can further comprise fragrances, preservatives, vitamins, ceramides, amino-acid derivatives, liposomes, polyols, such as glycerine and propylene glycol and botanicals (plant extracts) and additional conditioning agents such as quaternary polymers or silicone materials. Other additives can include, but are not limited to the following depending on the use, glycols, vitamins A, vitamin C and vitamin E in their various forms, Pro-Vitamin B5, sunscreen agents (these include those which absorb ultraviolet light between about 290-320 nanometers (the UV-B region) and those which absorb ultraviolet light in the range of 320-400 (the UV-B region)), humectants, preservatives, such as known parabens, emollients, occlusive agents, and esters. Other additives can include pigments especially when the emulsion is used as a make-up.

The compositions according to the invention can also contain agents for artificially tanning and/or browning the skin (self-tanning agents), such as, for example, dihydroxyacetone (DHA). These optional ingredients can be present in the emulsion compositions of this invention up in an amount of up to 5 parts by weight per 100 parts by weight of emulsion composition, but typically are present in amount of from 0.1 to 1 part by weight per 100 parts by weight of emulsion composition. Also the emulsion can be spray dried to form a resin/active composite particle.

The emulsion compositions of this invention may be prepared by mixing (or mechanically agitating) components (A)-(C), and any optional components, to form a homogenous mixture. This may be accomplished by any convenient mixing method known in the art exemplified by a spatula, mechanical stirrers, in-line mixing systems containing baffles and/or blades, powered in-line mixers, homogenizers, a drum roller, a three-roll mil, a sigma blade mixer, a bread dough mixer, and a two roll mill. The order of mixing is not considered critical.

EXAMPLES

Examples 1

Aminofunctional Silicone Resins A1-A9 were prepared in the following manner. A mixture of phenyltrimethoxysilane, phenylmethyldimethoxysilane, γ-aminopropyltriethoxysilane (APTES), and/or γ-aminopropyldiethoxymethylsilane (APDEMS) was optionally dissolved in aromatic solvent and hydrolyzed with deionized water, followed by distillative removal of by-product alcohol. The resulting structure was optionally reacted with trimethylethoxysilane, hexamethyldisilazane (HMDZ), APDEMS and/or dimethyldimethoxysilane, additional solvent and additional water added, a catalytic amount of aqueous potassium hydroxide optionally added and the water removed via azeotrope. The hydroxide, if added, was neutralized with aqueous HCl or acetic acid, and water removed again via azeotrope. The mixture was filtered and solvent removed to yield silicone resin product. The amount of each ingredient is shown in Table 1 below. The final aminofunctional silicone resin composition, wt % phenyl (Ph), wt % $R_2SiO$ (D), wt % $Me_2SiO$ (D(Me$_2$)), mole percent amino ($-CH_2CH_2CH_2NH_2$), wt % amine ($-NH_2$), and $-NH-$ (Amine H) equivalent weight are shown in Table 2 below.

Aminofunctional Silicone Resins B1-B6 were prepared in the following manner. Phenyltrimethoxysilane and/or phenylmethyldimethoxysilane, catalyzed by trifluoromethanesulfonic acid (TFMSA), were hydrolyzed with deionized water, followed by distillative removal of by-product alcohol. Hexamethyldisiloxane (HMDS) and additional water were added and the mixture heated to 50-60° C. optionally followed by distillative removal of volatiles. γ-Aminopropyltriethoxysilane (APTES) or γ-aminopropyldiethoxymethylsilane (APDEMS) were added along with additional water, followed by distillative removal of alcohol. Toluene, additional water and optionally a catalytic amount of 1.0 N aqueous potassium hydroxide were added and water removed via azeotrope. If added the hydroxide was neutralized with 1.0 N aqueous HCl, and water again removed via azeotrope. The mixture was filtered and solvent removed. The amount of each ingredient is shown in Table 1 below. The final aminofunctional silicone resin composition, wt % phenyl (Ph), wt % $R_2SiO$ (D), wt % $Me_2SiO$ (D(Me$_2$)), mole percent amino ($-CH_2CH_2CH_2NH_2$), wt % amine ($-NH_2$), and $-NH-$ (Amine H) equivalent weight are shown in Table 2 below.

Aminofunctional Silicone Resin C1 was prepared in the following manner. A mixture (amounts in Table 1) of phenyltrimethoxysilane, phenylmethyldimethoxysilane, and γ-aminopropyldiethoxymethylsilane (APDEMS) was optionally dissolved in xylenes and hydrolyzed with deionized water, followed by distillative removal of by-product alcohol. The resulting structure was reacted with trimethylethoxysilane, additional xylenes and additional water, followed by azeotropic removal of water. To a 177.0 gram portion of this reaction mixture, 19.3 grams of additional xylenes and 48.5 grams of colloidal silica dispersion (Ludox® HS-40-220 m$^2$/gm Grace Davison (Columbia, Md.)) were added and the water removed via azeotrope. The mixture was filtered and solvent removed to yield 110.6 grams of silicone resin product. The amount of each ingredient is shown in Table 1 below. The final aminofunctional silicone resin composition, wt % phenyl (Ph), wt % $R_2SiO$ (D), wt % $Me_2SiO$ (D(Me$_2$)), mole percent amino ($-CH_2CH_2CH_2NH_2$), wt % amine ($-NH_2$), and $-NH-$ (Amine H) equivalent weight are shown in Table 2 below.

Aminofunctional Siloxane Resin E1 was prepared in the following manner: A mixture of 119.6 g phenyltrimethoxysilane and 218.8 g phenylmethyldimethoxysilane were hydrolyzed with 67.3 g dilute aqueous HCl (0.02 N), followed by distillative removal of by-product methanol. The hydrolyzate was dissolved in 119.0 g toluene followed by azeotropic removal of residual water and subsequently reacted with 34.4 g cyclosilazane (1,1,2,4-Tetramethyl-1-sila-2-azacyclopentane). 5.1 g dilute aqueous KOH (1.0 N) was added and the mixture heated to reflux for three hours. The mixture was neutralized with 5.2 g aqueous HCl (1.0 N) dried via azeotropic distillation, filtered and solvent removed to yield 265.1 g of the silicone resin E1

TABLE 1

| | | | | | | | Weight (g) | | | | | | | |
|---|---|---|---|---|---|---|---|---|---|---|---|---|---|---|
| Ex. | PhSi(OMe)$_3$ | PhMeSi(OMe)$_2$ | APTES | APDEMS | Me$_3$SiOEt | HMDS | Xylene | Toluene | Water | TFMSA | 1.0 N KOH | 45% KOH | 1.0 N HCl | Yield (g) |
| A1 | 218.2 | 54.7 | | 76.6 | 35.5 | | 170.0 | | 90.1 | | | 4.8 | 4.9 | 237.0 |
| A2 | 277.7 | 255.6 | | 153.2 | 71.0 | | 343.8 | | 165.8 | | 9.6 | | 9.8 | 486.6 |
| A3 | 79.3 | 218.7 | | 76.7 | | | 175.1 | | 79.3 | | 4.9 | | 5.0 | 255.8 |

TABLE 1-continued

| Ex. | PhSi(OMe)$_3$ | PhMeSi(OMe)$_2$ | APTES | APDEMS | Me$_3$SiOEt | HMDS | Xylene | Toluene | Water | TFMSA | 1.0 N KOH | 45% KOH | 1.0 N HCl | Yield (g) |
|---|---|---|---|---|---|---|---|---|---|---|---|---|---|
| A4 | 158.7 | 145.9 |  | 76.6 |  |  | 173.0 |  | 86.5 |  | 4.9 |  | 5.0 | 250.5 |
| A5 | 99.2 | 237.0 |  | 38.3 |  |  | 178.0 |  | 81.1 |  | 5.0 |  | 5.0 | 258.8 |
| A6 | 178.5 |  | 110.7 | 77.4 | 35.5 |  | 161.8 |  | 71.7 |  |  |  |  | 219.9 |
| A7 | 198.4 |  |  | 153.4 |  |  | 164.9 |  | 88.4 |  |  |  |  | 233.9 |
| A8 | 138.8 | 91.4 |  | 153.5 |  |  | 168.8 |  | 84.8 |  | 4.7 |  | 4.8 | 240.4 |
| A9 | 138.8 | 55.0 |  | 191.3 |  |  | 165.8 |  | 84.8 |  | 4.7 |  | 4.8 | 213.3 |
| B1 | 99.1 | 146.2 | 66.4 |  |  | 34.1 |  | 163.0 | 72.1 | 0.12 | 4.5 |  | 4.4 | 182.8 |
| B2 | 205.3 |  |  | 88.0 |  | 78.4 |  | 117.6 | 72.5 | 0.14 |  |  |  | 242.4 |
| B3 | 208.2 | 76.7 |  | 40.2 |  | 35.8 |  | 168.9 | 79.6 | 0.13 | 4.7 |  | 4.6 | 246.5 |
| B4 | 218.1 | 40.1 |  | 42.1 |  | 56.3 |  | 169.4 | 75.3 | 0.13 | 4.9 |  | 4.8 | 245.7 |
| B5 | 208.4 | 57.5 |  | 40.2 |  | 44.8 |  | 165.3 | 75.7 | 0.12 | 4.7 |  | 4.6 | 239.5 |
| B6 | 208.2 | 38.3 |  | 80.4 |  | 35.8 |  | 167.2 | 79.5 | 0.12 | 4.7 |  | 4.6 | 184.5 |
| C1 | 277.7 | 255.6 |  | 153.1 | 71.0 |  | 343.0 |  | 165.8 |  |  |  |  |  |

TABLE 2

| Example | Aminofunctional Silicone Resin Comprising the Units | Wt % Ph# | wt % D* | wt % D(Me2) | Mol % Amino | wt % Amine | —NH— Eq. Wt. |
|---|---|---|---|---|---|---|---|
| A1 | $M_{0.079}D^{Ph}_{0.154}D^{NH2}_{0.203}T^{Ph}_{0.564}$ | 72.8 | 36.1 | 0.0 | 20 | 2.6 | 306 |
| A2 | $M_{0.095}D^{Ph}_{0.339}D^{NH2}_{0.206}T^{Ph}_{0.361}$ | 69.4 | 56.4 | 0.0 | 21 | 2.6 | 302 |
| A3 | $D^{Ph}_{0.592}D^{NH2}_{0.205}T^{Ph}_{0.201}$ | 71.9 | 80.1 | 0.0 | 20 | 2.5 | 320 |
| A4 | $D^{Ph}_{0.388}D^{NH2}_{0.206}T^{Ph}_{0.406}$ | 74.6 | 59.5 | 0.0 | 21 | 2.6 | 314 |
| A5 | $D^{Ph}_{0.628}D^{NH2}_{0.102}T^{Ph}_{0.267}$ | 80.3 | 73.9 | 0.0 | 10 | 1.2 | 645 |
| A6 | $M_{0.044}D^{NH2}_{0.207}T^{NH2}_{0.279}T^{Ph}_{0.461}$ | 51.6 | 20.5 | 0.0 | 49 | 6.6 | 123 |
| A7 | $M_{0.102}D^{NH2}_{0.400}T^{Ph}_{0.490}$ | 52.8 | 39.6 | 0.0 | 40 | 5.4 | 150 |
| A8 | $D^{Ph}_{0.250}D^{NH2}_{0.395}T^{Ph}_{0.352}$ | 58.7 | 63.8 | 0.0 | 40 | 5.0 | 160 |
| A9 | $D^{Ph}_{0.152}D^{NH2}_{0.499}T^{Ph}_{0.346}$ | 49.8 | 63.9 | 0.0 | 50 | 6.5 | 125 |
| B1 | $M_{0.176}D^{Ph}_{0.400}T^{NH2}_{0.151}T^{Ph}_{0.271}$ | 69.5 | 45.2 | 0.0 | 15 | 2.0 | 404 |
| B2 | $M_{0.355}D^{NH2}_{0.198}T^{Ph}_{0.441}$ | 52.7 | 21.3 | 0.0 | 20 | 2.9 | 279 |
| B3 | $M_{0.202}D^{Ph}_{0.199}D^{NH2}_{0.098}T^{Ph}_{0.496}$ | 73.6 | 30.1 | 0.0 | 10 | 1.4 | 613 |
| B4 | $M_{0.299}D^{Ph}_{0.101}D^{NH2}_{0.099}T^{Ph}_{0.497}$ | 67.5 | 22.3 | 0.0 | 10 | 1.4 | 581 |
| B5 | $M_{0.246}D^{Ph}_{0.150}D^{NH2}_{0.099}T^{Ph}_{0.501}$ | 70.8 | 27.4 | 0.0 | 10 | 1.4 | 595 |
| B6 | $M_{0.194}D^{Ph}_{0.101}D^{NH2}_{0.197}T^{Ph}_{0.502}$ | 65.3 | 31.4 | 0.0 | 20 | 2.7 | 301 |
| C1 | $M_{0.076}D^{Ph}_{0.341}D^{NH2}_{0.189}T^{Ph}_{0.332}Q_{0.059}$ | — | — | 69.9 | 56.6 | 0.0 | 323 |
| E1 | $M^{NH}_{0.115}D^{Ph}_{0.589}T^{Ph}_{0.293}$ | 84.7 | 27.8 | 0.0 | 11 | 0.7 | 1186 |

In Table 2 above:
molar mass of phenyl in the composition divided by the molar mass of all resin R groups in the composition
*based on the molar mass of the designated group divided by the molar mass of the composition
M denotes $(CH_3)_3SiO_{1/2}$
$M^{NH}$ denotes $(CH_3)_2RSiO_{1/2}$ where R = —$CH_2(CH_3)CHCH_2NHCH_3$
D denotes $(CH_3)_2SiO_{2/2}$
$D^{Ph}$ denotes $C_6H_5(CH_3)SiO_{2/2}$
$D^{NH2}$ denotes $(CH_3)RSiO_{2/2}$ where R = —$CH_2CH_2CH_2NH_2$
$T^{Ph}$ denotes $C_6H_5SiO_{3/2}$
$T^{NH2}$ denotes $RSiO_{3/2}$ where R = —$CH_2CH_2CH_2NH_2$
Q denotes $SiO_{4/2}$

Example 2

30.0 g of aminofunctional silicone resin B4 prepared and described above comprising the units $M_{0.299}$ $D^{Ph}_{0.101}$ $D^{NH2}_{0.099}$ $T^{Ph}_{0.497}$ wherein M, $D^{Ph}$, $D^{NH2}$, and $T^{Ph}$ are as defined above, was weighed into a Hauschild (Hamm, Germany) Max 40 plastic cup followed by 0.9 g of Tergitol® TMN-6 (2,6,8-trimethyl-4-nonyloxypolyethylene oxyethanol (6 EO) a nonionic surfactant from The Dow Chemical Company (Midland, Mich.)), 1.0 g Tergitol® 15-S-30 (alkylene-oxypolyethylene oxyethanol ($C_{11-15}$ secondary alkyl, 30 EO) a nonionic surfactant from The Dow Chemical Company (Midland, Mich.) and 2.0 g of deionized water. The cup was closed and placed into a Hauschild (Hamm, Germany) Speedmixer™ DAC-150 laboratory mixing device. The cup and its contents were cycled in the mixer for 20 seconds. The cup was opened and the walls of the cup were scraped with a spatula. The cup and its contents were subjected to a second 20 second mixing cycle. Next 6 g of DI water was added and the cup was again subjected to a 20 second mixing cycle. An additional 10 g of DI water was added in increments of 5 g followed by a 20 second mixing cycle after each addition. The emulsion that resulted was milky white in appearance with a slight bluish tint. The emulsion consisted of an approximately 60% by weight resin oil particle phase. Mean particle size was measured using a Microtrac® (Montgomeryville, Pa.) UPA150 instrument and had the following properties: D(v, 0.5)=0.2766 um, D(v, 0.9)=0.3467 um

Example 3

1.02 g of amino functional siloxane resin E1 was weighed into a glass vial followed by the addition of 5.68 g of DER® 331 and 3.35 g Versamine® C-30. The ingredients were mixed thoroughly with a wooden stir rod resulting in a clear and colorless mixture containing 10% by weight of siloxane resin E1 and stoichiometric ratio of amine to epoxy. Six mil drawdowns were made onto Chromated aluminum panels (AL-39 from Q-Panel Inc. Cleveland, Ohio) and the panels were exposed to a nitrogen purged oven for one hour at 100° C. and one hour at 150° C. The cured film was clear and colorless and had increased flexibility (4) compared to a control sample (6) with no siloxane resin added as measured by T Bend Flex Test (ASTM D4145).

The invention claimed is:

1. An aminofunctional silicone resin comprising the units:
$(R_3SiO_{1/2})_a$ (i)
$(R_2SiO_{2/2})_b$ (ii)
$(RSiO_{3/2})_c$ (iii) and
$(SiO_{4/2})_d$ (iv)
wherein R is independently an alkyl group, an aryl group, or an aminofunctional hydrocarbon group, a has a value of less than 0.4, b has a value of greater than 0.15, c has a value of greater than zero to 0.7, d has a value of less than 0.2, the value of a+b+c+d=1, with the provisos that 3 to 50 mole percent of silicon atoms contain aminofunctional hydrocarbon groups in units (i), (ii) or (iii), the —NH— equivalent weight of the aminofunctional silicone resin is from 100 to 1500, the aminofunctional silicone resin is in the form of a neat liquid, solution, or meltable solid, greater than 20 weight percent of unit (ii) is present in the aminofunctional silicone resin, less than 10 weight percent of unit (ii) are $Me_2SiO_{2/2}$ units in the aminofunctional silicone resin, and greater than 50 weight percent of silicon-bonded R groups are silicon-bonded aryl groups.

2. An aminofunctional silicone resin comprising the units:
$(R_3SiO_{1/2})_a$ (i)
$(R_2SiO_{2/2})_b$ (ii)
$(RSiO_{3/2})_c$ (iii) and
$(SiO_{4/2})_d$ (iv)
wherein R is independently an alkyl group, an aryl group, or an aminofunctional hydrocarbon group, a has a value of less than 0.4, b has a value of greater than 0.15, c has a value of greater than zero to 0.7, d has a value of less than 0.2, the value of a+b+c+d=1, with the provisos that 3 to 50 mole percent of silicon atoms contain aminofunctional hydrocarbon groups in units (i), (ii) or (iii), the —NH— equivalent weight of the aminofunctional silicone resin is from 100 to 1000, the aminofunctional silicone resin is in the form of a neat liquid, solution, or meltable solid, greater than 20 weight percent of unit (ii) is present in the aminofunctional silicone resin, less than 10 weight percent of unit (ii) are $Me_2SiO_{2/2}$ units in the aminofunctional silicone resin, and greater than 50 weight percent of silicon-bonded R groups are silicon-bonded aryl groups.

3. An aminofunctional silicone resin according to claim 1 wherein R is independently selected from methyl, phenyl, or an aminofunctional hydrocarbon group having the formula $R^1NHR^2$ or —$R^1NHR^1NHR^2$ wherein each $R^1$ is independently a divalent hydrocarbon radical having at least 2 carbon atoms and $R^2$ is hydrogen or an alkyl group.

4. An aminofunctional silicone resin according to claim 1 wherein the aminofunctional hydrocarbon groups are selected from —$CH_2CH_2NH_2$, —$CH_2CH_2CH_2NH_2$, —$CH_2CHCH_3NH$, —$CH_2CH_2CH_2CH_2NH_2$, —$CH_2CH_2CH_2CH_2CH_2NH_2$, —$CH_2CH_2CH_2CH_2CH_2CH_2NH_2$, —$CH_2CH_2NHCH_3$, —$CH_2CH_2CH_2NHCH_3$, —$CH_2(CH_3)CHCH_2NHCH_3$, —$CH_2CH_2CH_2CH_2NHCH_3$, —$CH_2CH_2NHCH_2CH_2NH_2$, —$CH_2CH_2CH_2NHCH_2CH_2NH_2$, —$CH_2CH_2CH_2CH_2NHCH_2CH_2CH_2NH_2$, —$CH_2CH_2NHCH_2CH_2NHCH_3$, —$CH_2CH_2CH_2NHCH_2CH_2NHCH_3$, —$CH_2CH_2CH_2CH_2NHCH_2CH_2CH_2NHCH_3$, and —$CH_2CH_2NHCH_2CH_2NHCH_2CH_2CH_3$—.

5. An aminofunctional resin according to claim 1 wherein the aminofunctional silicone resin is selected from
aminofunctional silicone resins comprising the units:
 (i) $((CH_3)_3SiO_{1/2})_a$
 (ii) $(C_6H_5(CH_3)SiO_{2/2})_b$
 (iii) $((CH_3)RSiO_{2/2})_b$ where R=—$CH_2CH_2CH_2NH_2$
 (iv) $(C_6H_5SiO_{3/2})_c$,
aminofunctional silicone resins comprising the units:
 (i) $(C_6H_5(CH_3)SiO_{2/2})_b$
 (ii) $((CH_3)RSiO_{2/2})_b$ where R=—$CH_2CH_2CH_2NH_2$
 (iii) $(C_6H_5SiO_{3/2})_c$,
aminofunctional silicone resins comprising the units:
 (i) $((CH_3)_3SiO_{1/2})_a$
 (ii) $((CH_3)RSiO_{2/2})_b$ where R=—$CH_2CH_2CH_2NH_2$
 (iii) $(RSiO_{3/2})_c$ where R=—$CH_2CH_2CH_2NH_2$
 (iv) $(C_6H_5SiO_{3/2})_c$,
aminofunctional silicone resins comprising the units:
 (i) $((CH_3)_3SiO_{1/2})_a$
 (ii) $((CH_3)RSiO_{2/2})_b$ where R=—$CH_2CH_2CH_2NH_2$
 (iii) $(C_6H_5SiO_{3/2})_c$ or
aminofunctional silicone resins comprising the units:
 (i) $((CH_3)_3SiO_{1/2})_a$
 (ii) $(C_6H_5(CH_3)SiO_{2/2})_b$
 (iii) $((CH_3)RSiO_{2/2})_b$ where R=—$CH_2CH_2CH_2NH_2$
 (iv) $(C_6H_5SiO_{3/2})_c$
 (v) $(SiO_{4/2})_d$
wherein a, b, c, and d are as defined above.

6. An aminofunctional resin according to claim 1 wherein the aminofunctional silicone resin is selected from aminofunctional silicone resins comprising the units:
 (i) $((CH_3)_3SiO_{1/2})_a$
 (ii) $(C_6H_5(CH_3)SiO_{2/2})_b$
 (iii) $((CH_3)RSiO_{2/2})_b$ where R=—$CH_2CH_2CH_2NH_2$
 (iv) $(C_6H_5SiO_{3/2})_c$,
aminofunctional silicone resins comprising the units:
 (i) $(C_6H_5(CH_3)SiO_{2/2})_b$
 (ii) $((CH_3)RSiO_{2/2})_b$ where R=—$CH_2CH_2CH_2NH_2$
 (iii) $(C_6H_5SiO_{3/2})_c$,
aminofunctional silicone resins comprising the units:
 (i) $((CH_3)_3SiO_{1/2})_a$
 (ii) $((CH_3)RSiO_{2/2})_b$ where R=—$CH_2CH_2CH_2NH_2$
 (iii) $(RSiO_{3/2})_c$ where R=—$CH_2CH_2CH_2NH_2$
 (iv) $(C_6H_5SiO_{3/2})_c$,
aminofunctional silicone resins comprising the units:
 (i) $((CH_3)_3SiO_{1/2})_a$
 (ii) $((CH_3)RSiO_{2/2})_b$ where R=—$CH_2CH_2CH_2NH_2$
 (iii) $(C_6H_5SiO_{3/2})_c$
aminofunctional silicone resin comprising the units
 (i) $((CH_3)_3SiO_{1/2})_a$
 (ii) $(CH_3)_2SiO_{2/2})_b$
 (iii) $((CH_3)RSiO_{2/2})_b$ where R=—$CH_2CH_2CH_2NH_2$
 (iv) $(C_6H_5SiO_{3/2})_c$
aminofunctional silicone resin comprising the units:
 (i) $((CH_3)_2RSiO_{1/2})_a$ where R=—$CH_2(CH_3)CHCH_2NHCH_3$
 (ii) $(CH_3)_2SiO_{2/2})_b$
 (iii) $(C_6H_5(CH_3)SiO_{2/2})_b$
 (iv) $(C_6H_5SiO_{3/2})_c$
aminofunctional silicone resins comprising the units:
 (i) $((CH_3)_2RSiO_{1/2})_a$ where R=—$CH_2(CH_3)CHCH_2NHCH_3$
 (ii) $(C_6H_5(CH_3)SiO_{2/2})_b$
 (iii) $(C_6H_5SiO_{3/2})_c$,
aminofunctional silicone resins comprising the units:

(i) $((CH_3)RSiO_{2/2})_b$ where $R=-CH_2(CH_3)CHCH_2NHCH_3$
(ii) $(C_6H_5(CH_3)SiO_{2/2})_b$
(iii) $(C_6H_5SiO_{3/2})_c$,
aminofunctional silicone resins comprising the units:
(i) $((CH_3)_2RSiO_{1/2})_a$ where $R=-CH_2(CH_3)CHCH_2NHCH_3$
(ii) $(C_6H_5(CH_3)SiO_{2/2})_b$
(iii) $(SiO_{4/2})_d$, or
aminofunctional silicone resins comprising the units:
(i) $((CH_3)_3SiO_{1/2})_a$
(ii) $(C_6H_5(CH_3)SiO_{2/2})_b$
(iii) $((CH_3)RSiO_{2/2})_b$ where $R=-CH_2CH_2CH_2NH_2$
(iv) $(C_6H_5SiO_{3/2})_c$
(v) $(SiO_{4/2})_d$
wherein a, b, c, and d are as defined above.

7. An emulsion composition comprising:
(A) an aminofunctional silicone resin comprising the units:
$(R_3SiO_{1/2})_a$ (i)
$(R_2SiO_{2/2})_b$ (ii)
$(RSiO_{3/2})_c$ (iii) and
$(SiO_{4/2})_d$ (iv)
wherein R is independently an alkyl group, an aryl group, or an aminofunctional hydrocarbon group, a has a value of less than 0.4, b has a value of greater than 0.15, c has a value of greater than zero to 0.7, d has a value of less than 0.2, the value of a+b+c+d=1, with the provisos that 3 to 50 mole percent of silicon atoms contain aminofunctional hydrocarbon groups in units (i), (ii) or (iii), the —NH— equivalent weight of the aminofunctional silicone resin is from 100 to 1500, the aminofunctional silicone resin is in the form of a neat liquid, solution, or meltable solid, greater than 20 weight percent of unit (ii) is present in the aminofunctional silicone resin, less than 10 weight percent of unit (ii) are $Me_2SiO_{2/2}$ units in the aminofunctional silicone resin, and greater than 50 weight percent of silicon-bonded R groups are silicon-bonded aryl groups;
(B) at least one surfactant; and
(C) water.

8. An emulsion composition according to claim 7 wherein a has a value of 0.1 to 0.3, b has a value of 0.2 to 0.4, c has a value of 0.2 to 0.5, d has a value of 0, 10 to 30 mole percent of silicon atoms contain aminofunctional hydrocarbon groups in units (i), (ii) or (iii), the —NH— equivalent weight of the aminofunctional silicone resin is from 150 to 350, 20 to 50 weight percent of unit (ii) is present in the aminofunctional silicone resin, 0 to 5 weight percent of unit (ii) are $Me_2SiO_{2/2}$ units in the aminofunctional silicone resin, and from 50 to 75 weight percent of silicon-bonded R groups are silicon-bonded aryl groups.

9. An emulsion composition according to claim 7 wherein the surfactant is selected from anionic surfactants, cationic surfactants, nonionic surfactants, amphoteric surfactants, or a combination thereof.

10. An emulsion composition according to claim 7, wherein the emulsion composition further comprises at least one ingredient selected from fragrances, preservatives, vitamins, ceramides, amino-acid derivatives, liposomes, polyols, botanicals, conditioning agents, glycols, vitamin A, vitamin C, vitamin B, Pro-Vitamin B5, sunscreen agents, humectants, preservatives, emollients, occlusive agents, esters, pigments, or self-tanning agents.

11. An emulsion composition according to claim 7, wherein the emulsion is in the form of spray-dried composite particles.

12. An aminofunctional silicone resin according to claim 2 wherein R is independently selected from methyl, phenyl, or an aminofunctional hydrocarbon group having the formula $R^1NHR^2$ or $-R^1NHR^1NHR^2$ wherein each $R^1$ is independently a divalent hydrocarbon radical having at least 2 carbon atoms and $R^2$ is hydrogen or an alkyl group.

13. An aminofunctional silicone resin according to claim 2 wherein the aminofunctional hydrocarbon groups are selected from $-CH_2CH_2NH_2$, $-CH_2CH_2CH_2NH_2$, $-CH_2CHCH_3NH$, $-CH_2CH_2CH_2CH_2NH_2$, $-CH_2CH_2CH_2CH_2CH_2NH_2$, $-CH_2CH_2CH_2CH_2CH_2CH_2NH_2$, $-CH_2CH_2NHCH_3$, $-CH_2CH_2CH_2NHCH_3$, $-CH_2(CH_3)CHCH_2NHCH_3$, $-CH_2CH_2CH_2CH_2NHCH_3$, $-CH_2CH_2NHCH_2CH_2NH_2$, $-CH_2CH_2CH_2NHCH_2CH_2NH_2$, $-CH_2CH_2CH_2CH_2NHCH_2CH_2CH_2NH_2$, $-CH_2CH_2NHCH_2CH_2NHCH_3$, $-CH_2CH_2CH_2NHCH_2CH_2NHCH_3$, $-CH_2CH_2CH_2CH_2NHCH_2CH_2CH_2CH_2NHCH_3$, and $-CH_2CH_2NHCH_2CH_2NHCH_2CH_2CH_3-$.

14. An aminofunctional resin according to claim 2 wherein the aminofunctional silicone resin is selected from
aminofunctional silicone resins comprising the units:
(i) $((CH_3)_3SiO_{1/2})_a$
(ii) $(C_6H_5(CH_3)SiO_{2/2})_b$
(iii) $((CH_3)RSiO_{2/2})_b$ where $R=-CH_2CH_2CH_2NH_2$
(iv) $(C_6H_5SiO_{3/2})_c$,
aminofunctional silicone resins comprising the units:
(i) $(C_6H_5(CH_3)SiO_{2/2})_b$
(ii) $((CH_3)RSiO_{2/2})_b$ where $R=-CH_2CH_2CH_2NH_2$
(iii) $(C_6H_5SiO_{3/2})_c$,
aminofunctional silicone resins comprising the units:
(i) $((CH_3)_3SiO_{1/2})_a$
(ii) $((CH_3)RSiO_{2/2})_b$ where $R=-CH_2CH_2CH_2NH_2$
(iii) $(RSiO_{3/2})_c$ where $R=-CH_2CH_2CH_2NH_2$
(iv) $(C_6H_5SiO_{3/2})_c$,
aminofunctional silicone resins comprising the units:
(i) $((CH_3)_3SiO_{1/2})_a$
(ii) $((CH_3)RSiO_{2/2})_b$ where $R=-CH_2CH_2CH_2NH_2$
(iii) $(C_6H_5SiO_{3/2})_c$ or
aminofunctional silicone resins comprising the units:
(i) $((CH_3)_3SiO_{1/2})_a$
(ii) $(C_6H_5(CH_3)SiO_{2/2})_b$
(iii) $((CH_3)RSiO_{2/2})_b$ where $R=-CH_2CH_2CH_2NH_2$
(iv) $(C_6H_5SiO_{3/2})_c$
(v) $(SiO_{4/2})_d$
wherein a, b, c, and d are as defined above.

15. An aminofunctional resin according to claim 2 wherein the aminofunctional silicone resin is selected from aminofunctional silicone resins comprising the units:
(i) $((CH_3)_3SiO_{1/2})_a$
(ii) $(C_6H_5(CH_3)SiO_{2/2})_b$
(iii) $((CH_3)RSiO_{2/2})_b$ where $R=-CH_2CH_2CH_2NH_2$
(iv) $(C_6H_5SiO_{3/2})_c$,
aminofunctional silicone resins comprising the units:
(i) $(C_6H_5(CH_3)SiO_{2/2})_b$
(ii) $((CH_3)RSiO_{2/2})_b$ where $R=-CH_2CH_2CH_2NH_2$
(iii) $(C_6H_5SiO_{3/2})_c$,
aminofunctional silicone resins comprising the units:
(i) $((CH_3)_3SiO_{1/2})_a$
(ii) $((CH_3)RSiO_{2/2})_b$ where $R=-CH_2CH_2CH_2NH_2$
(iii) $(RSiO_{3/2})_c$ where $R=-CH_2CH_2CH_2NH_2$
(iv) $(C_6H_5SiO_{3/2})_c$,
aminofunctional silicone resins comprising the units:
(i) $((CH_3)_3SiO_{1/2})_a$
(ii) $((CH_3)RSiO_{2/2})_b$ where $R=-CH_2CH_2CH_2NH_2$
(iii) $(C_6H_5SiO_{3/2})_c$
aminofunctional silicone resin comprising the units
(i) $((CH_3)_3SiO_{1/2})_a$
(ii) $(CH_3)_2SiO_{2/2})_b$ (iii) $((CH_3)RSiO_{2/2})_b$ where $R=-CH_2CH_2CH_2NH_2$
(iv) $(C_6H_5SiO_{3/2})_c$
aminofunctional silicone resin comprising the units:
(i) $((CH_3)_2RSiO_{1/2})_a$ where $R=-CH_2(CH_3)CHCH_2NHCH_3$
(ii) $(CH_3)_2SiO_{2/2})_b$
(iii) $(C_6H_5(CH_3)SiO_{2/2})_b$
(iv) $(C_6H_5SiO_{3/2})_c$
aminofunctional silicone resins comprising the units:
(i) $((CH_3)_2RSiO_{1/2})_a$ where $R=-CH_2(CH_3)CHCH_2NHCH_3$
(ii) $(C_6H_5(CH_3)SiO_{2/2})_b$
(iii) $(C_6H_5SiO_{3/2})_c$,
aminofunctional silicone resins comprising the units:
(i) $((CH_3)RSiO_{2/2})_b$ where $R=-CH_2(CH_3)CHCH_2NHCH_3$
(ii) $(C_6H_5(CH_3)SiO_{2/2})_b$
(iii) $(C_6H_5SiO_{3/2})_c$,
aminofunctional silicone resins comprising the units:
(i) $((CH_3)_2RSiO_{1/2})_a$ where $R=-CH_2(CH_3)CHCH_2NHCH_3$
(ii) $(C_6H_5(CH_3)SiO_{2/2})_b$
(iii) $(SiO_{4/2})_d$, or
aminofunctional silicone resins comprising the units:
(i) $((CH_3)_3SiO_{1/2})_a$
(ii) $(C_6H_5(CH_3)SiO_{2/2})_b$
(iii) $((CH_3)RSiO_{2/2})_b$ where $R=-CH_2CH_2CH_2NH_2$
(iv) $(C_6H_5SiO_{3/2})_c$
(v) $(SiO_{4/2})_d$
wherein a, b, c, and d are as defined above.

16. An emulsion composition comprising:
(A) an aminofunctional silicone resin comprising the units:
$(R_3SiO_{1/2})_a$ (i)
$(R_2SiO_{2/2})_b$ (ii)
$(RSiO_{3/2})_c$ (iii) and
$(SiO_{4/2})_d$ (iv)
wherein R is independently an alkyl group, an aryl group, or an aminofunctional hydrocarbon group, a has a value of less than 0.4, b has a value of greater than 0.15, c has a value of greater than zero to 0.7, d has a value of less than 0.2, the value of a+b=c+d=1, with the provisos that 3 to 50 mole percent of silicon atoms contain aminofunctional hydrocarbon groups in units (i), (ii) or (iii), the —NH— equivalent weight of the aminofunctional silicone resin is from 100 to 1000, the aminofunctional silicone resin is in the form of a neat liquid, solution, or meltable solid, greater than 20 weight percent of unit (ii) is present in the aminofunctional silicone resin, less than 10 weight percent of unit (ii) are $Me_2SiO_{2/2}$ units in the aminofunctional silicone resin, and greater than 50 weight percent of silicon-bonded R groups are silicon-bonded aryl groups;
(B) at least one surfactant; and
(C) water.

17. An emulsion composition according to claim 16 wherein a has a value of 0.1 to 0.3, b has a value of 0.2 to 0.4, c has a value of 0.2 to 0.5, d has a value of 0, 10 to 30 mole percent of silicon atoms contain aminofunctional hydrocarbon groups in units (i), (ii) or (iii), the —NH— equivalent weight of the aminofunctional silicone resin is from 150 to 350, 20 to 50 weight percent of unit (ii) is present in the aminofunctional silicone resin, 0 to 5 weight percent of unit (ii) are $Me_2SiO_{2/2}$ units in the aminofunctional silicone resin, and from 50 to 75 weight percent of silicon-bonded R groups are silicon-bonded aryl groups.

18. An emulsion composition according to claim 16 wherein the surfactant is selected from anionic surfactants, cationic surfactants, nonionic surfactants, amphoteric surfactants, or a combination thereof.

19. An emulsion composition according to any of claims 16, wherein the emulsion composition further comprises at least one ingredient selected from fragrances, preservatives, vitamins, ceramides, amino-acid derivatives, liposomes, polyols, botanicals, conditioning agents, glycols, vitamin A, vitamin C, vitamin E, Pro-Vitamin B5, sunscreen agents, humectants, preservatives, emollients, occlusive agents, esters, pigments, or self-tanning agents.

20. An emulsion composition according to any of claims 16, wherein the emulsion is in the form of spray-dried composite particles.

* * * * *